(12) United States Patent
Kawaguchi (10) Patent No.: US 10,172,542 B2
(45) Date of Patent: Jan. 8, 2019

(54) MOTOR PERFORMANCE EVALUATION APPARATUS, MOTOR PERFORMANCE EVALUATION SYSTEM, AND MOTOR PERFORMANCE EVALUATION METHOD

(71) Applicant: TOYO UNIVERSITY, Bunkyo-ku, Tokyo (JP)

(72) Inventor: Hideo Kawaguchi, Hatoyama-machi (JP)

(73) Assignee: TOYO UNIVERSITY, Tokyo (JP)

( * ) Notice: Subject to any disclaimer, the term of this patent is extended or adjusted under 35 U.S.C. 154(b) by 430 days.

(21) Appl. No.: 14/979,669

(22) Filed: Dec. 28, 2015

(65) Prior Publication Data
US 2016/0183848 A1    Jun. 30, 2016

(30) Foreign Application Priority Data

Dec. 24, 2014    (JP) .................................. 2014-259818

(51) Int. Cl.
*A61B 5/00*    (2006.01)
*A61B 5/11*    (2006.01)

(52) U.S. Cl.
CPC ............ *A61B 5/1124* (2013.01); *A61B 5/1126* (2013.01); *A61B 5/4082* (2013.01); *A61B 5/4094* (2013.01); *A61B 2562/0219* (2013.01)

(58) Field of Classification Search
CPC ....... A61B 5/11; A61B 5/1101; A61B 5/1124; A61B 5/1125
See application file for complete search history.

(56) References Cited

U.S. PATENT DOCUMENTS 9,005,133 B2 *   4/2015   Zietsma ............... A61B 5/1101
                                                    600/407
9,186,095 B2 *   11/2015  Machado ............. A61B 5/6897

FOREIGN PATENT DOCUMENTS

JP    2009-101108 A    5/2009
JP    2010-131280 A    6/2010

OTHER PUBLICATIONS

Ishizuka, Tokutake, Neddachi and Kawaguchi, "Development of an evaluation method for analyzing the motor performance of elderly people using handwriting features", Journal of the Visualization Society of Japan, Jul. 1, 2014, 49-50, 34-1, Japan
Kawaguchi, "Research for Quantification Method of Motor Performance of Elderly People", New Technology Presentation Meeting, Sep. 26, 2014, Japan.

(Continued)

*Primary Examiner* — Max Hindenburg
(74) *Attorney, Agent, or Firm* — Metrolexis Law Group, PLLC (57) ABSTRACT

A motor performance evaluation apparatus 100 for evaluating motor performance of a subject, including: an acquisition unit 131 configured to acquire drawing stroke information including position information and time information on drawing stroke of the subject copying a predetermined single-stroke drawn figure; a detection unit 132 configured to detect a fall count indicating the number of times a drawing acceleration of the subject changes from a positive value to a negative value, based on the drawing stroke information; and an evaluation unit 133 configured to evaluate the motor performance of the subject, based on the fall count.

5 Claims, 4 Drawing Sheets

(56) References Cited

OTHER PUBLICATIONS

Kawaguchi, "Can we predict the risks of mental health disorders and falls of elderly using handwriting characteristics?", Indiana University Presentation, Oct. 22, 2015. U.S.A.
English translation of Certificate Letter "Proving Document for seeking Application of Provision of Exceptions to Lack of Novelty of Invention" which was filed with Japanese Patent Office (JPO) on Jan. 22, 2015.
English translation of Certificate Document 1 "Proving Document for seeking Application of Provision of Exceptions to Lack of Novelty of Invention" which was filed with JPO on Jan. 22, 2015 for Discloser of Jul. 1, 2014: the document reported in "Proceedings of the 42nd Visualization Symposium, vol. 34 Suppl., No. 1, 2014" published by the Visualization Society of Japan.
English translation of Certificate Document 2 "Proving Document for seeking Application of Provision of Exceptions to Lack of Novelty of Invention" which was filed with JPO on Jan. 22, 2015 for Discloser of Sep. 26, 2014: the inventor presented at "the Briefing Meeting of New Technologies" sponsored by Toyo University Incorporated Educational Institution.
Certificate "Proving Document for seeking Application of Provision of Exceptions to Lack of Novelty of Invention" filed with JPO on Jan. 22, 2015, with References: Ishizaki et al. "Development of an evaluation . . . ", Jornal of the Visualization Society of Japan, Jul. 1, 2014, 49-50, 34-1; and Kawaguchi "Research for Quantification Method of . . . ", New Technology Presentation Meeting, Sep. 26, 2014, Japan.
Corrected English translation of Ishizaki et al. "Development of an evaluation method for analyzing the motor performance of elderly people using handwriting features" Journal of the Visualization Society of Japan, Jul. 1, 2014, 49-50, 34-1, Japan.

* cited by examiner

MOTOR PERFORMANCE EVALUATION APPARATUS, MOTOR PERFORMANCE EVALUATION SYSTEM, AND MOTOR PERFORMANCE EVALUATION METHOD

CROSS REFERENCE TO RELATED APPLICATIONS

This application is based upon and claims the benefit of priority from prior Japanese Patent Application No. 2014-259818, filed on Dec. 24, 2014; the entire contents of which are incorporated herein by reference.

BACKGROUND OF THE INVENTION

1. Field of the Invention

The present invention relates to a motor performance evaluation apparatus, a motor performance evaluation system, and a motor performance evaluation method for evaluating motor performance of a subject.

2. Description of the Related Art

In the field of life sciences, an approach for evaluating motor performance has heretofore been researched and developed.

For example, Patent Literature 1 (Japanese Patent Application Publication No. 2009-101108) discloses a technology capable of evaluating motor performance. Specifically, the technology disclosed in Patent Literature 1 involves making a subject perform a posture changing motion such as a side-to-side twisting motion or a forward bending motion, and measuring an acceleration component and a geomagnetic component while the subject is performing such a motion. Then, the motor performance of the subject is determined from the amount of posture change calculated based on measured results.

Meanwhile, Patent Literature 2 (Japanese Patent Application Publication No. 2010-131280) discloses a technology capable of evaluating a mental or psychological state of a subject, although not evaluating motor performance. Specifically, the technology disclosed in Patent Literature 2 involves extracting the height, width, area, or the like of a letter or picture, as a feature value, based on temporal and spatial information on a subject's handwritten letter or hand-drawn picture, and determining the mental or psychological state of the subject from the extracted feature value.

However, the conventional technologies pose problems as given below.

Although being capable of evaluating the motor performance, the technology according to Patent Literature 1 needs the subject to perform the posture changing motion or the like. Thus, a heavy work load is imposed on the subject if the subject is an aged person, a sick person, or the like, for example.

Meanwhile, the technology according to Patent Literature 2 is incapable of evaluating the motor performance of the subject, although this technology is advantageous in terms of reduction in the work load on the subject as compared to the technology according to Patent Literature 1, because of merely making the subject perform the simple work of writing a letter or drawing a picture by hand.

Thus, in the conventional technologies, there has not been established a technology for evaluating the motor performance of the subject while reducing the work load imposed on the subject, and hence there is a desire for a solution to the problems.

SUMMARY OF THE INVENTION

In view of the above circumstances, the inventor has made the following studies. Specifically, the inventor has pursued the studies while considering that if motor performance of a subject can be evaluated from subject's drawing stroke, it enables reducing a work load imposed on the subject and also allows a simple method to evaluate the motor performance of the subject. Consequently, the inventor has made the present invention after making the findings that when the subject is drawing a figure with a single stroke, there is a correlation between the motor performance and a fall count indicating the number of times a drawing acceleration changes from a positive value to a negative value.

A first aspect of the present invention is a motor performance evaluation apparatus for evaluating motor performance of a subject, including: an acquisition unit configured to acquire drawing stroke information including position information and time information on drawing stroke of the subject copying a predetermined single-stroke drawn figure; a detection unit configured to detect a fall count indicating the number of times a drawing acceleration of the subject changes from a positive value to a negative value, based on the drawing stroke information; and an evaluation unit configured to evaluate the motor performance of the subject, based on the fall count.

A second aspect of the present invention is the motor performance evaluation apparatus according to the above-described aspect, in which the predetermined single-stroke drawn figure is a figure including rectangular and triangular waves repeated alternately with each other.

A third aspect of the present invention is the motor performance evaluation apparatus according to the above-described aspect, in which the drawing stroke information includes stroke pressure information indicating a stroke pressure, and the detection unit determines position information and time information on a single-stroke drawn portion included in the drawing stroke, based on the stroke pressure information, and detects the fall count based on the determined position information and time information on the single-stroke drawn portion.

A fourth aspect of the present invention is a motor performance evaluation system for evaluating motor performance of a subject, including: a measuring unit configured to measure position information and time information on drawing stroke of the subject copying a predetermined single-stroke drawn figure; an acquisition unit configured to acquire drawing stroke information including the position information and the time information on the drawing stroke, measured by the measuring unit; a detection unit configured to detect a fall count indicating the number of times a drawing acceleration of the subject changes from a positive value to a negative value, based on the drawing stroke information; and an evaluation unit configured to evaluate the motor performance of the subject, based on the fall count.

A fifth aspect of the present invention is a motor performance evaluation method using a motor performance evaluation apparatus for evaluating motor performance of a subject, including the steps of: acquiring drawing stroke information including position information and time information on drawing stroke of the subject copying a predetermined single-stroke drawn figure; detecting a fall count indicating the number of times a drawing acceleration of the subject changes from a positive value to a negative value, based on the drawing stroke information; and evaluating the motor performance of the subject, based on the fall count.

DETAILED DESCRIPTION OF THE EMBODIMENTS

A first embodiment will be described below with reference to the drawings.

[First Embodiment]

(Configuration of Motor Performance Evaluation System 1)

Figure 1:
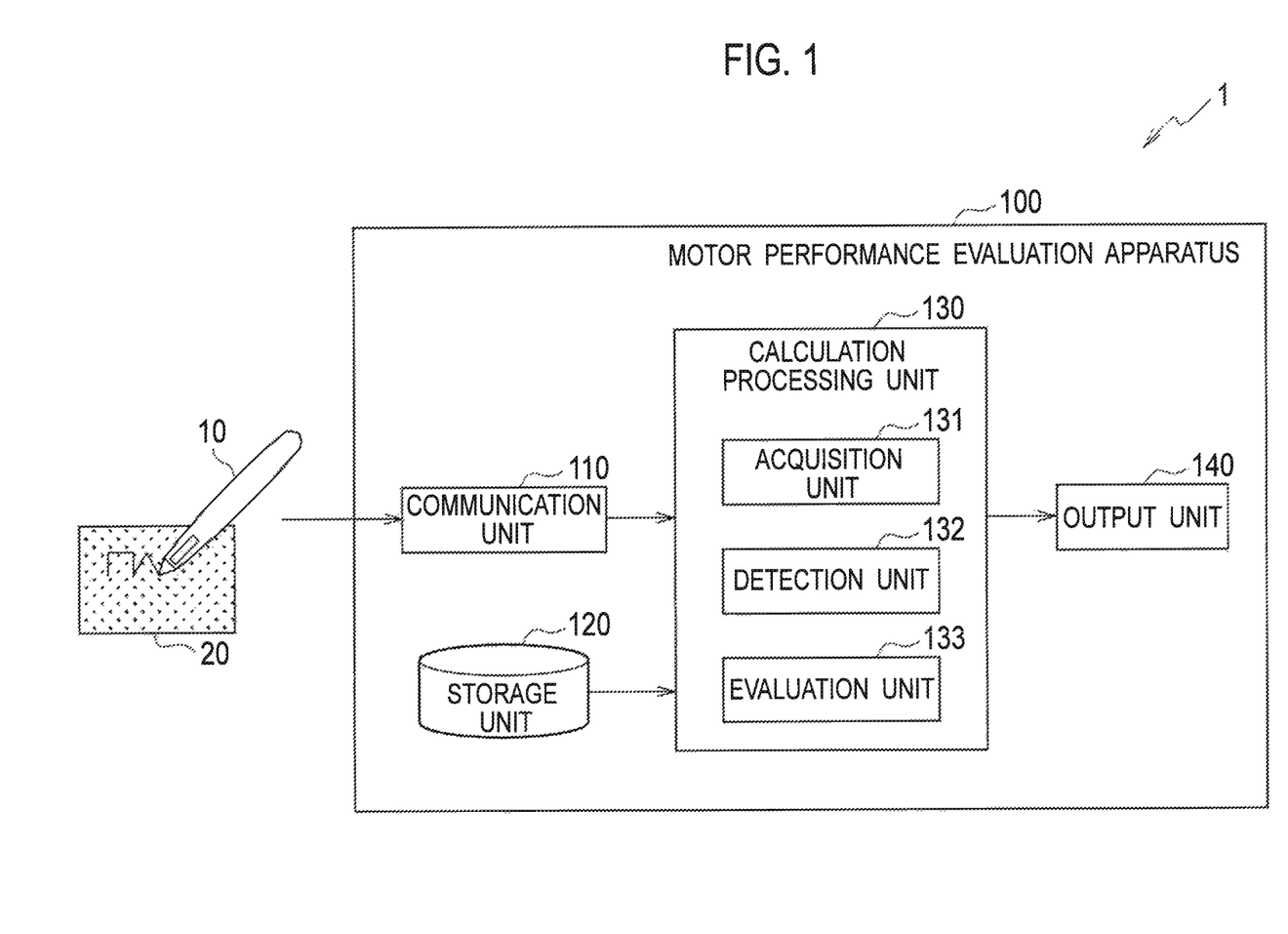
FIG. 1 is a schematic diagram illustrating a configuration of a motor performance evaluation system according to a first embodiment.

FIG. 1 is a schematic diagram illustrating a configuration of a motor performance evaluation system 1 according to the first embodiment. The motor performance evaluation system 1 according to the first embodiment evaluates motor performance of a subject. In the embodiment, the motor performance refers to performance indicating MFS (Motor Fitness Scale: muscular strength, mobility, or balance) and/or PMF (Physical and Motor Function: a grip advantage, a timed up and go test, etc.).

As illustrated in FIG. 1, the motor performance evaluation system 1 according to the first embodiment includes a drawing stroke measuring device 10 and a motor performance evaluation apparatus 100.

The drawing stroke measuring device 10 measures position information and time information on drawing stroke of a subject copying a predetermined single-stroke drawn figure. In the embodiment, the predetermined single-stroke drawn figure is a figure including rectangular and triangular waves repeated alternately with each other in a predetermined direction (refer to FIG. 3A). The predetermined single-stroke drawn figure will be described in detail later.

The drawing stroke measuring device 10 includes a position sensor and an internal clock (not illustrated), and measures the drawing stroke position information and the drawing stroke time information corresponding to the position information at predetermined sampling periods, when the subject draws the figure on an entry sheet 20. The shorter predetermined sampling period is desirable because of higher resolution. For example, the predetermined sampling period may be set within a range of 60 to 80 Hz, or may be set to 70 Hz.

The drawing stroke measuring device 10 generates drawing stroke information including the drawing stroke position information and the time information corresponding to the position information measured at predetermined sampling periods. The drawing stroke information generated by the drawing stroke measuring device 10 is transmitted to the motor performance evaluation apparatus 100.

The timing of transmission of the drawing stroke information is not particularly limited. The drawing stroke measuring device 10 may store the drawing stroke information in a memory (not illustrated) and transmit the stored drawing stroke information at a predetermined time.

A well-known technology such as the technology disclosed in Japanese Patent Application Publication No. 2010-131280 may be applied to the above-mentioned drawing stroke measuring device 10. Moreover, the drawing stroke measuring device 10 may be constructed of a digital pen, may be constructed of a mouse, or may be constructed of a touch panel. In the embodiment, the drawing stroke measuring device 10 forms a measuring unit in the motor performance evaluation system 1.

The motor performance evaluation apparatus 100 includes a communication unit 110, a storage unit 120, a calculation processing unit 130, and an output unit 140.

The communication unit 110 communicates with the drawing stroke measuring device 10. Communication between the communication unit 110 and the drawing stroke measuring device 10 may be wire communication or radio communication and is not particularly limited. The communication unit 110 receives the drawing stroke information transmitted from the drawing stroke measuring device 10 and outputs the drawing stroke information to the calculation processing unit 130.

The storage unit 120 is constructed of a storage medium such as a hard disk or a memory. The storage unit 120 stores various types of information required for the motor performance evaluation apparatus 100 to perform processing.

The calculation processing unit 130 controls various functions of the motor performance evaluation apparatus 100. The calculation processing unit 130 is a calculation module constructed of hardware such as a processor such as a CPU or a DSP (Digital Signal Processor), a memory, and other electronic circuits, or software such as a program having the function, or a combination of these. The calculation module appropriately loads and executes the program to virtually construct various functional modules, and uses the constructed functional modules to perform various types of processing on operation control of parts or user operation.

The output unit 140 functions as a display and displays output information from the calculation processing unit 130. The output unit 140 may be configured to print the output information, or may be configured to transmit the output information to an external device (for example, an external PC).

(Configuration of Calculation Processing Unit 130)

Next, a configuration of the calculation processing unit 130 will be described. The calculation processing unit 130 according to the embodiment includes an acquisition unit 131, a detection unit 132, and an evaluation unit 133.

The acquisition unit 131 acquires the position information and the time information on the drawing stroke of the subject copying the predetermined single-stroke drawn figure. Specifically, the acquisition unit 131 acquires the drawing stroke information from the drawing stroke measuring device 10 via the communication unit 110.

The detection unit 132 detects a fall count indicating the number of times a drawing acceleration of the subject changes from a positive value to a negative value, based on the drawing stroke information. Specifically, the detection unit 132 arranges, in time series, the position information and the time information included in the drawing stroke information by the acquisition unit 131, and calculates the drawing acceleration. Then, the detection unit 132 detects the fall count indicating the number of fall portions in which the drawing acceleration changes from the positive value to the negative value, based on the drawing acceleration arranged in time series.

The evaluation unit 133 evaluates motor performance of the subject, based on the fall count. Here, there is a correlation between the fall count and the individual motor performance. Therefore, the evaluation unit 133 uses the fall count as an index value of the motor performance to evaluate (or estimate) the motor performance of the subject.

For example, the evaluation unit 133 may cause the storage unit 120 to prestore an age-based correlation table having a correspondence between the fall count and the age-based motor performance, and may refer to the age-based correlation table stored in the storage unit 120 to evaluate the age according to the motor performance of the subject from the fall count.

The evaluation unit 133 outputs evaluated results to the output unit 140. For example, the evaluation unit 133 causes the output unit 140 to display the fall count as the index value of the motor performance. Alternatively, the evaluation unit 133 may operate in the following manner: the evaluation unit 133 determines whether or not the fall count is equal to or more than a predetermined evaluation threshold, and if the fall count is equal to or more than the predetermined evaluation threshold, the evaluation unit 133 outputs information for the output unit 140 to display "○ (GOOD)," or if the fall count is less than the predetermined evaluation threshold, the evaluation unit 133 outputs information for the output unit 140 to display "x (NO GOOD)."

(Operation of Motor Performance Evaluation Apparatus)

Figure 2:
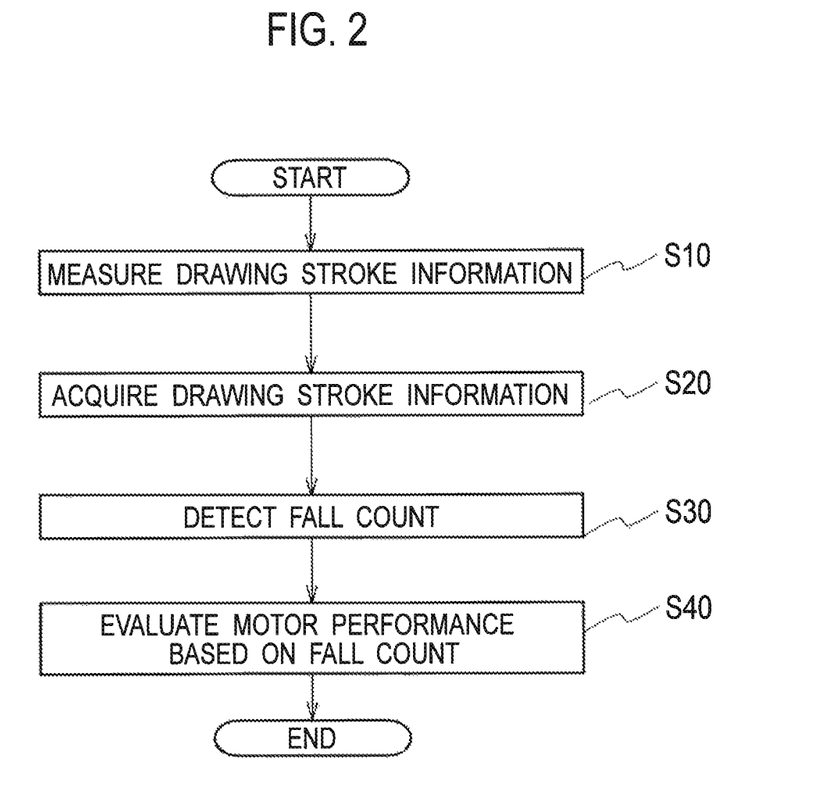
FIG. 2 is a flowchart illustrating operation of the motor performance evaluation system according to the first embodiment.

Next, operation of the motor performance evaluation system 1 will be described. FIG. 2 is a flowchart illustrating operation which the motor performance evaluation system 1 performs to acquire drawing stroke information.

At step S10, the drawing stroke measuring device 10 measures position information and time information on drawing stroke of a subject copying a predetermined single-stroke drawn figure. Here, FIG. 3A is an explanatory diagram illustrating an example of a predetermined single-stroke drawn figure, and FIG. 3B is an explanatory diagram illustrating an example of subject's drawing stroke.

Figure 3A:
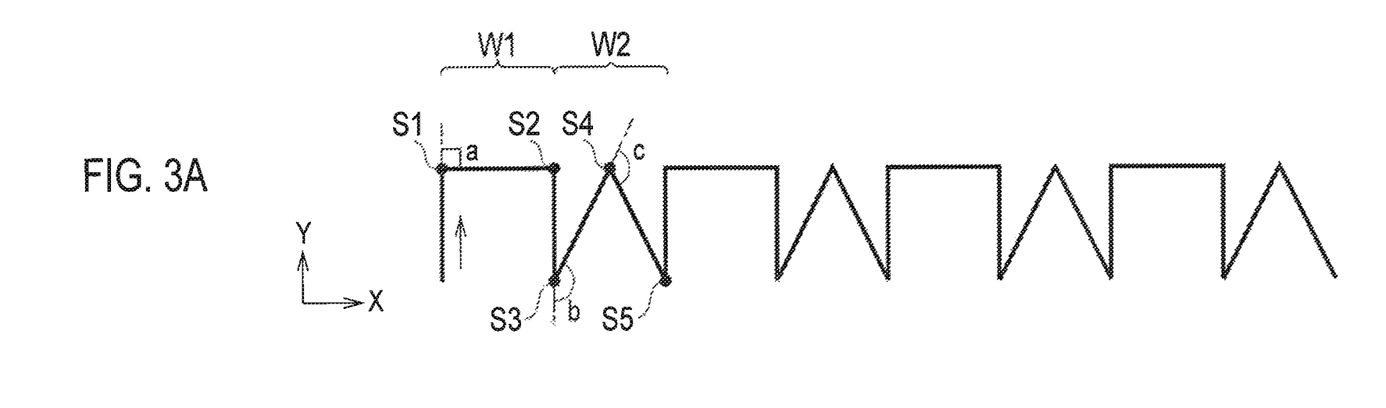
FIG. 3A is an explanatory diagram illustrating an example of a single-stroke drawn figure according to the first embodiment.

As illustrated in FIG. 3A, the predetermined single-stroke drawn figure according to the embodiment is a figure including rectangular waves W2 and triangular waves W1 repeated alternately with each other in a predetermined direction. In other words, the predetermined single-stroke drawn figure may be said to be a figure formed of plural lines connected together, and connection portions S1 to S5 form angles. Also, preferably, the angles in the connection portions S1 to S5 are not identical. For example, an angle a of the connection portions S1 and S2 is 90°, an angle b of the connection portions S3 and S5 is 150°, and an angle c of the connection portion S4 is 120°.

Figure 3B:
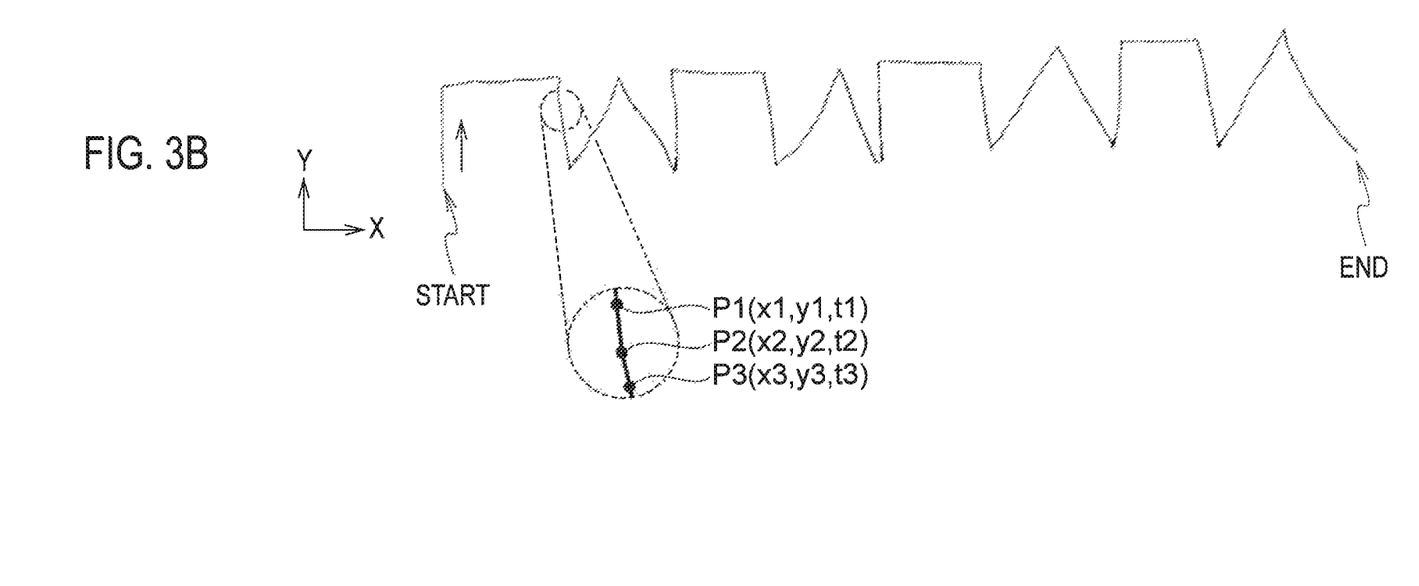
FIG. 3B is an explanatory diagram illustrating an example of drawing stroke according to the first embodiment.

The subject copies the predetermined single-stroke drawn figure thereby to draw a single-stroke copied figure as illustrated in FIG. 3B. At this time, the subject draws the single-stroke copied figure in a single stroke (or one stroke). Preferably, the single-stroke copied figure includes at least two or more (or two or more sets of) copied shapes of rectangular waves W1 and triangular waves W2, or more preferably three or more (or three or more sets of) copied shapes.

When the subject is copying the predetermined single-stroke drawn figure, the drawing stroke measuring device 10 generates information including position information and time information on drawing stroke of the single-stroke copied figure drawn by the subject, and transmits the generated information to the motor performance evaluation apparatus 100.

Specifically, the drawing stroke measuring device 10 measures the position information and the time information at predetermined sampling periods and generates drawing stroke information P1 to P3, as illustrated in FIG. 3B. In FIG. 3B, x1 to x3 and y1 to y3 included in the drawing stroke information P1 to P3 indicate coordinate values on an x-y plane, and t1 to t3 indicate time. Also, the drawing stroke measuring device 10 transmits the generated drawing stroke information P1 to P3 to the motor performance evaluation apparatus 100.

At step S20, in the motor performance evaluation apparatus 100, the acquisition unit 131 acquires the drawing stroke information via the communication unit 110.

At step S30, the detection unit 132 detects a fall count indicating the number of times the drawing acceleration of the subject changes from a positive value to a negative value, based on the drawing stroke information. Specifically, the detection unit 132 arranges, in time series, the position information and the time information included in the drawing stroke information, and calculates speed information. Then, the detection unit 132 calculates the drawing acceleration, based on the speed information arranged in time series.

Figure 4:
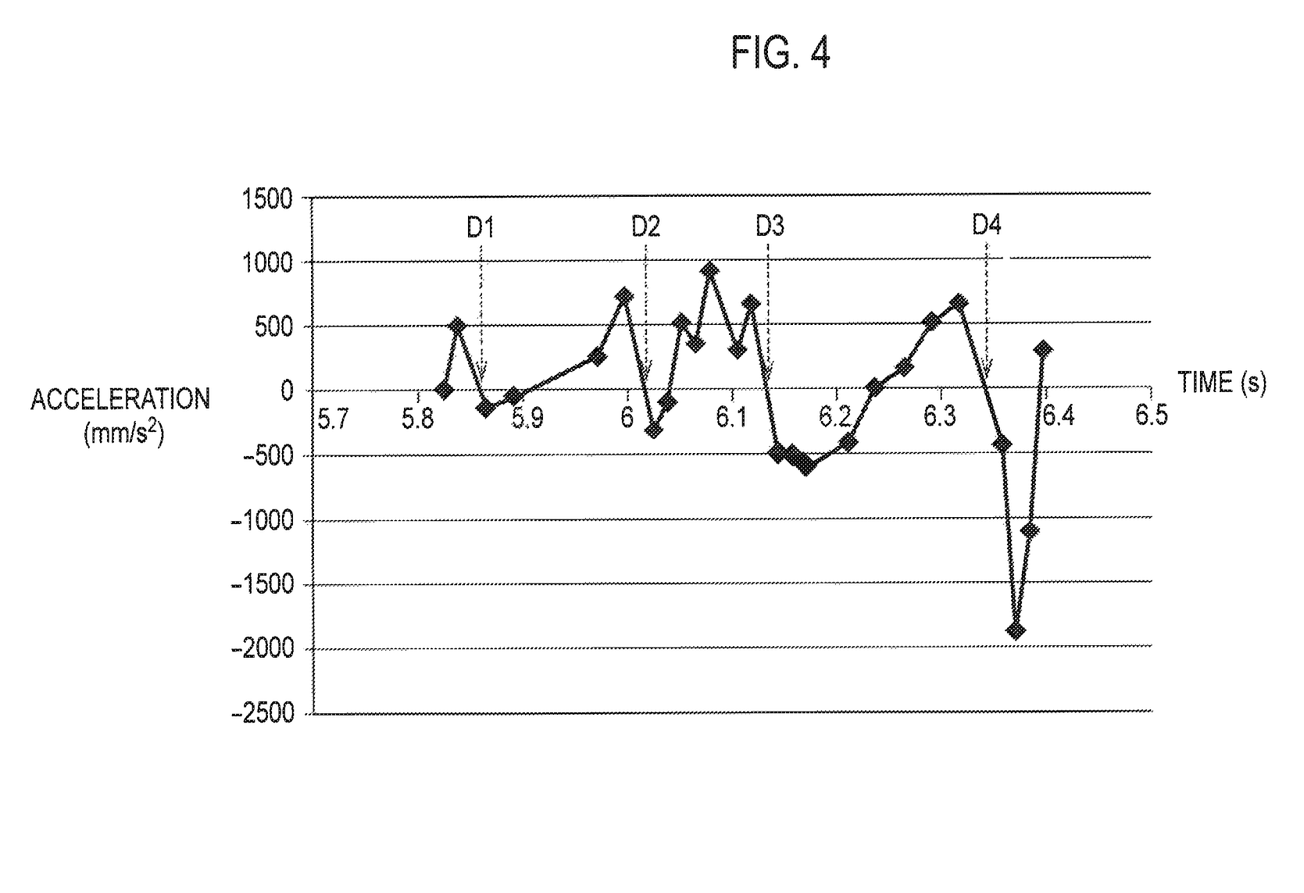
FIG. 4 is a graph illustrating an example of a relationship between time information and a drawing acceleration calculated based on drawing stroke information according to the first embodiment.

Here, FIG. 4 illustrates an example of a graph illustrating a relationship between the time information and the drawing acceleration calculated by the detection unit 132. As illustrated in FIG. 4, the detection unit 132 detects the fall count indicating the number of times the drawing acceleration changes from a positive value to a negative value, based on the acceleration information arranged in time series. In the example of FIG. 4, fall portions are indicated by D1 to D4, and the fall count is four.

At step S40, the evaluation unit 133 evaluates the motor performance of the subject, based on the fall count. Specifically, the evaluation unit 133 uses the fall count as the index value of the motor performance to evaluate (or estimate) the motor performance of the subject. Also, at step S40, the evaluation unit 133 outputs evaluated results to the output unit 140.

(Function and Effect)

As described above, in the motor performance evaluation system 1 according to the first embodiment, the motor performance evaluation apparatus 100 includes the detection unit 132 configured to detect the fall count indicating the number of times the drawing acceleration of the subject changes from a positive value to a negative value, based on the drawing stroke information, and the evaluation unit 133 configured to evaluate the motor performance of the subject, based on the fall count.

Here, the drawing stroke information includes the position information and the time information on the drawing stroke of the subject copying the predetermined single-stroke drawn figure, and can be acquired by the subject copying the predetermined single-stroke drawn figure. In other words, the drawing stroke information is information which can be acquired by a simple method.

As described above, according to the motor performance evaluation system 1 according to the first embodiment, the motor performance of the subject can be evaluated from the fall count detected from the drawing stroke information, and thus, this enables reducing a work load imposed on the subject and also allows a simple method to evaluate the motor performance of the subject, without imposing a work load on the subject, such as making the subject perform a posture changing motion.

The motor performance evaluation system 1 according to the first embodiment enables reducing the work load imposed on the subject, and thus is advantageous when the subject is an aged person, a sick person, or the like, for example. Further, the motor performance evaluation system 1 is effective for diagnosis of sarcopenia indicating a decrease in muscular strength involved in aging, or a decrease in the amount of muscle involved in aging.

Moreover, in the embodiment, the predetermined single-stroke drawn figure is a figure including rectangular and triangular waves repeated alternately with each other. Such a figure is prone to increase the fall count included in drawing stroke, as compared to a figure having a simple repetitions such as a figure including repeated rectangular waves or triangular waves. In other words, such a figure is prone to develop a close correlation between the fall count and the motor performance of the subject, and thus, this figure is preferable for evaluation of the motor performance, as compared to other figures, which in turn enables more accurate evaluation of the motor performance.

[Modification 1]

Next, Modification 1 of the motor performance evaluation system 1 according to the first embodiment will be described.

Here, it is also possible that when copying a predetermined single-stroke drawn figure, a subject cannot draw the entire figure in a single stroke (or one stroke) and separates the drawing stroke measuring device 10 from the entry sheet 20. In such a case, the subject does not draw the single-stroke copied figure in a single stroke (or one stroke), and thus, the accuracy of position information and time information included in drawing stroke information acquired by the motor performance evaluation apparatus 100 may be insufficient to evaluate the motor performance.

Assuming the above-mentioned case, in this embodiment, the drawing stroke measuring device 10 further includes a stroke pressure sensor for measuring a stroke pressure. The drawing stroke measuring device 10 generates drawing stroke information including stroke pressure information indicating the stroke pressure, in addition to position information and time information, at predetermined sampling periods.

Moreover, the detection unit 132 according to the embodiment determines position information and time information on a single-stroke drawn portion included in drawing stroke, based on the stroke pressure information, and detects a fall count based on the determined position information and time information on the single-stroke drawn portion.

Specifically, the detection unit 132 determines the drawing stroke information including the stroke pressure information indicating a value indicating that the drawing stroke measuring device 10 is in contact with the entry sheet 20, based on the stroke pressure information. The detection unit 132 determines that a drawing stroke information group consisting of a series of items of the drawing stroke information is the drawing stroke information corresponding to the single-stroke drawn portion.

Thus, the detection unit 132 determines the drawing stroke information corresponding to the single-stroke drawn portion (or a one-stroke portion) included in the drawing stroke, based on the stroke pressure information, thereby to determine the position information and the time information included in the drawing stroke information. Then, the detection unit 132 detects the fall count based on the drawing stroke information corresponding to the single-stroke drawn portion.

Meanwhile, if the stroke pressure information indicates a value (for example, "0 Pa") indicating that the drawing stroke measuring device 10 is not in contact with the entry sheet 20, the detection unit 132 excludes the drawing stroke information including the stroke pressure information.

In the motor performance evaluation system 1 according to the embodiment, as described above, the motor performance evaluation apparatus 100 determines the drawing stroke information corresponding to the single-stroke drawn portion (or the one-stroke portion) included in the drawing stroke, based on the stroke pressure information, and detects the fall count indicating the number of times the drawing acceleration changes from a positive value to a negative value, based on the position information and the time information included in the drawing stroke information.

Thus, the motor performance evaluation apparatus 100 detects the fall count based on the drawing stroke information corresponding to the single-stroke drawn portion drawn with a single stroke (or in one stroke), thus enabling more accurate evaluation of the motor performance of the subject.

[Modification 2]

Next, description will be given with regard to Modification 2 of the motor performance evaluation system 1 according to the first embodiment. In the above-mentioned first embodiment, the evaluation unit 133 uses the fall count as the index value of the motor performance; however, the evaluation unit 133 may calculate the index value based on the fall count and information other than the fall count.

In this embodiment, for example, the evaluation unit 133 calculates a total drawing stroke distance, a total stop time, and a total entry time, based on the position information and the time information included in the drawing stroke information, and calculates the index value of the motor performance, based on one or more of these pieces of calculated information and on the fall count.

Note that the total drawing stroke distance indicates a total distance of a single-stroke drawn figure drawn by the subject with a single stroke (or in one stroke). The total stop time indicates a total time of stop of the position information when the subject is drawing. The total entry time indicates a period of time during which the subject draws a single-stroke copy figure.

Moreover, if the drawing stroke information includes the stroke pressure information, the evaluation unit 133 may calculate the index value based on the fall count and the stroke pressure information. In other words, the evaluation unit 133 may calculate the index value of the motor performance, based on any one or more of the total drawing stroke distance, the total stop time, the total entry time and the stroke pressure and on the fall count.

In the embodiment, as described above, the evaluation unit 133 calculates the index value based on the fall count and the information other than the fall count, and evaluates (or estimates) the motor performance of the subject, based on the calculated index value, thus enabling more accurate evaluation of the motor performance of the subject.

[Example]

Next, description will be given with regard to Example. First, physical measurements and motor tests for measuring motor performance were conducted on plural adult men and women as subjects, thereby to acquire actual measured values of the motor performance Specifically, measurements were performed on the plural adult men and women as the subjects, to measure their heights, blood pressures, physical fats, weights, grips, BMI, skeletal muscle ratios, subcutaneous fats, girths of abdomens, open-eye one-leg standing times, TUG (Timed Up and Go), and the like. Then, measured values of the motor performance for grip advantages (advantages of left and right grips), MFS (mobility), MFS (balance), total MFS (a total of mobility, balance and muscular strength), and TUG were acquired based on measured values.

Meanwhile, calculations of the index values of the motor performance were performed on the same plural adult men and women as the subjects, by using the motor performance evaluation system 1 according to this embodiment. The index values of the motor performance were calculated for the grip advantages (the advantages of left and right grips), MFS (the mobility), MFS (the balance), the total MFS (the total of the mobility, the balance and the muscular strength), and TUG Then, correlation coefficients r between actual measured values of the motor performance acquired by actual measurement and the index values of the motor performance acquired by using the motor performance evaluation system 1 were calculated.

Tables 1 to 2 represent the correlation coefficients r between the index values of the motor performance and the actual measured values of the motor performance. Specifically, Table 1 represents the correlation coefficients of the adult men as the subjects, and Table 2 represents the correlation coefficients of the adult women as the subjects.

In Table 1, skeletal muscle indices (SMI) of the adult men were calculated based on Equation (1), and skeletal muscle indices (SMI) of the adult women were calculated based on Equation (2).

$$\text{SMI (kg/m}^2\text{)} = 0.326 \times (\text{BMI}) - 0.047 \times (\text{girth of abdomen}) - 0.011 \times (\text{age}) + 5.135 \quad (1)$$

$$\text{SMI (kg/m}^2\text{)} = 0.156 \times (\text{BMI}) + 0.044 \times (\text{grip}) - 0.010 \times (\text{girth of abdomen}) + 2.747 \quad (2)$$

TABLE 1

| MFS · PMF | Equation for calculation of index value of motor performance based on drawing stroke information | Correlation coefficient |
| --- | --- | --- |
| Grip average (kg) | Acceleration fall count | r = −0.73 |
| MFS (mobility) | Average stroke pressure/total stop time | r = −0.83 |
| MFS (balance) | Acceleration fall count/total entry time | r = −0.71 |
| Total MFS | Acceleration fall count/total stop time | r = −0.87 |
| Grip average (kg) | Acceleration fall count/total stop time | r = −0.92 |

TABLE 2

| MFS · PMF | Equation for calculation of index value of motor performance based on drawing stroke information | Correlation coefficient |
| --- | --- | --- |
| MFS (muscular strength) | Acceleration fall count | r = 0.36 |
| MFS (balance) | Acceleration fall count | r = 0.43 |
| Total MFS | Acceleration fall count | r = 0.43 |
| SMI (kg/m$^2$) | Acceleration fall count | r = −0.55 |
| MFS (mobility) | Average stroke pressure/acceleration fall count | r = −0.52 |
| MFS (muscular strength) | Average stroke pressure/acceleration fall count | r = −0.53 |
| MFS (balance) | Average stroke pressure/acceleration fall count | r = −0.64 |
| Total MFS | Average stroke pressure/acceleration fall count | r = −0.65 |
| Grip average (kg) | Actual average speed/total stop time | r = 0.58 |
| TUG (s) | Average stroke pressure/acceleration fall count | r = 0.45 |
| SMI (kg/m$^2$) | Total drawing stroke distance/acceleration fall count | r = 0.79 |

As illustrated in Tables 1 and 2, the presence of a sufficient correlation between the index values of the motor performance and the actual measured value of the motor performance was proved based on the correlation coefficients between the index values of the motor performance and the actual measured value of the motor performance. It has been proved that the index values of the motor performance calculated by using the motor performance evaluation system 1 according to the embodiment have a sufficient correlation for evaluation of the motor performance.

[Other Embodiments]

Although the present invention has been described in detail by using the above-mentioned embodiment, it is apparent to those skilled in the art that the present invention is not limited to the embodiment described herein.

For example, in the above-mentioned embodiment, the drawing stroke measuring device 10 is configured to generate drawing stroke information; however, the motor performance evaluation apparatus 100 may generate drawing stroke information. For example, the drawing stroke measuring device 10 may transmit position information and time information to the motor performance evaluation apparatus 100, and the acquisition unit 131 of the motor performance evaluation apparatus 100 may generate drawing stroke information including the position information and the time information.

Moreover, in the above-described embodiment, the predetermined single-stroke drawn figure is described by giving the figure including the rectangular and triangular waves repeated alternately with each other as an example, as illustrated in FIG. 3A; however, a figure for use in a DAL (Draw a Line slowly) test may be applied.

As described above, it is to be understood that the present invention is not limited to the above-described embodiments as they are, and in stages of practice, structural elements may be modified and embodied without departing from the scope of the subject matter of the invention. Moreover, various inventions may be formed by suitable combinations of plural structural elements disclosed in the above-described embodiments. For example, some structural elements may be excluded from all structural elements disclosed in the embodiments.

What is claimed is:

1. A motor performance evaluation apparatus for evaluating motor performance of a subject, comprising:
an acquisition unit configured to acquire drawing stroke information including position information and time information on drawing stroke of the subject copying a predetermined single-stroke drawn figure at a predetermined sampling period;
a detection unit configured to detect a fall count indicating the number of times a drawing acceleration of the subject changes from a positive value to a negative value, based on the drawing stroke information acquired at the predetermined sampling period;

a storage unit configured to prestore an age-based correlation table having a correspondence between the fall count and the age-based motor performance;

an evaluation unit configured to evaluate the motor performance of the subject, based on the fall count with the age-based correlation table; and an output unit configured to display output information evaluated by the evaluation unit.

2. The motor performance evaluation apparatus according to claim 1, wherein the predetermined single-stroke drawn figure is a figure including rectangular and triangular waves repeated alternately with each other.

3. The motor performance evaluation apparatus according to claim 1, wherein the drawing stroke information includes stroke pressure information indicating a stroke pressure, and the detection unit determines position information and time information on a single-stroke drawn portion included in the drawing stroke, based on the stroke pressure information, and detects the fall count based on the determined position information and time information on the single-stroke drawn portion.

4. A motor performance evaluation system for evaluating motor performance of a subject, comprising:

a measuring unit configured to measure position information and time information on drawing stroke of the subject copying a predetermined single-stroke drawn figure at a predetermined sampling period;

an acquisition unit configured to acquire drawing stroke information including the position information and the time information on the drawing stroke, measured by the measuring unit at the predetermined sampling period;

a detection unit configured to detect a fall count indicating the number of times a drawing acceleration of the subject changes from a positive value to a negative value, based on the drawing stroke information;

a storage unit configured to prestore an age-based correlation table having a correspondence between the fall count and the age-based motor performance;

an evaluation unit configured to evaluate the motor performance of the subject, based on the fall count with the age-based correlation table; and an output unit configured to display output information evaluated by the evaluation unit.

5. A motor performance evaluation method using a motor performance evaluation apparatus for evaluating motor performance of a subject, comprising:

acquiring drawing stroke information including position information and time information on drawing stroke of the subject copying a predetermined single-stroke drawn figure at a predetermined sampling period;

detecting a fall count indicating the number of times a drawing acceleration of the subject changes from a positive value to a negative value, based on the drawing stroke information acquired at the predetermined sampling period;

prestoring an age-based correlation table having a correspondence between the fall count and the age-based motor performance to a storage unit;

evaluating the motor performance of the subject, based on the fall count with the age-based correlation table; and displaying output information evaluated by an evaluation unit to an output unit.

* * * * *